Figure 1:
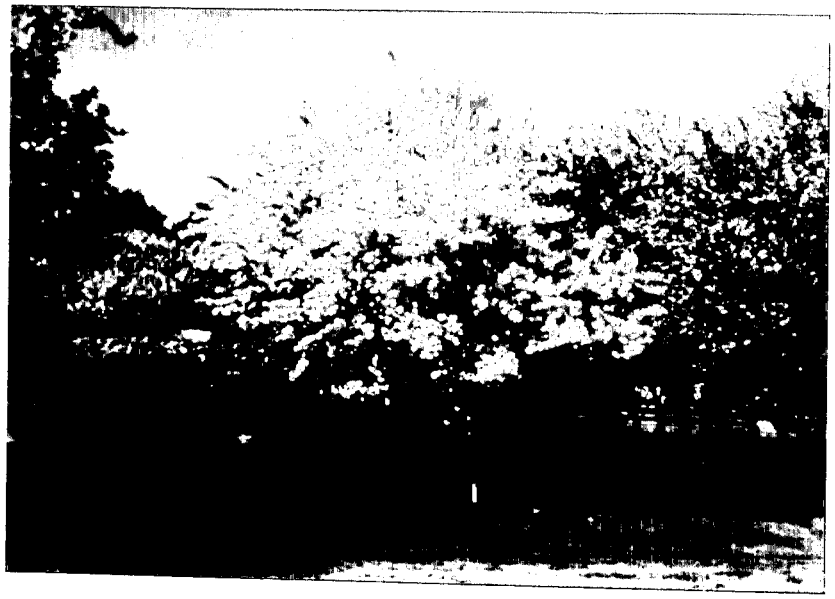
Figure 2:
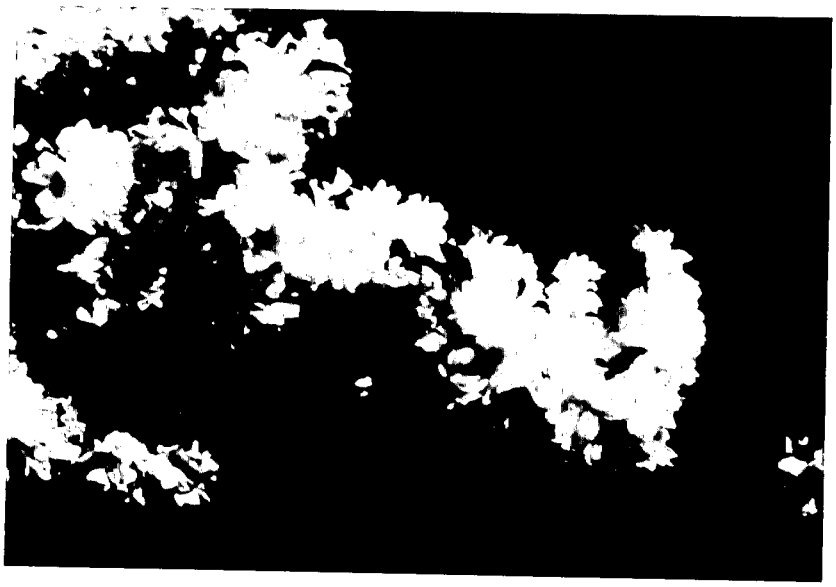

United States Patent [19]

Flemer, III

[11] Patent Number: Plant 5,800

[45] Date of Patent: Nov. 18, 1986

[54] FLOWERING CRAB APPLE TREE

[75] Inventor: William Flemer, III, Princeton, N.J.

[73] Assignee: Treesearch, Kingston, N.J.

[21] Appl. No.: 664,202

[22] Filed: Oct. 24, 1984

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Frank B. Robb

[57] ABSTRACT

A flowering Crab Apple Tree denominated "Bridal Bouquet" selected from a block of seedlings of Malus "Katherine," an unpatented variety, which seedling was noted as having abundant, large size, pure white-colored double flowers and in continued growth the leaves have been unaffected by Apple Scab disease or Fire Blight disease, even in wet summers, and thus die-back is not caused such as is experienced by standard Japanese Crab and Tea varieties.

2 Drawing Figures

My present invention relates to a new and distinct variety of flowering Crab Apple Tree which was discovered by me as a seedling in a block of open pollinated seedlings of the Malus variety "Katherine" (an unpatented variety) which block of seedlings were growing in a nursery at Kingston, N.J.

I have carried on a series of programs of tree hybridization over a number of years and this particular variety is deemed to be outstanding in my opinion as a new and improved variety of flowering crab and particularly notable because of the abundance, large size and pure white color of the double flowers produced.

I have therefore determined that the variety shall be known as "Bridal Bouquet" because of the foregoing and the same will be identified hereinafter thereby, exhibiting as it does a number of outstanding characteristics which make the same worthy of continued development and certainly planting and production for decorative purposes.

The variety has been asexually reproduced by me by bud grafting and progeny have exhibited the same floral characteristics as well as others to be subsequently referred to.

In the years during which the tree has been reproduced and grown, when other varieties of crab apple trees of the same age and growing in adjacent rows were badly defoliated by Apple Scab disease, the leaves of this variety were not affected.

It is notable that the parent tree as well as the progeny have exhibited no evidence of Fire Blight disease even though they have grown through wet summers when standard varieties such as the Japanese Crab (*Malus floribunda*) and Tea Crab (*Malus hupehensis*) suffered considerable die back.

As may be said to be typical of flowering crabs, the fruits of this variety are not abundant or especially colorful and therefore the question of fruiting is relatively unimportant.

It is emphasized that the asexual reproduction heretofore referred to which has taken place in South Brunswick Township, N.J., discloses that the characteristics which are set forth in detail and distinctions noted come true to form and are established and transmitted through the succeeding propagations.

In one drawing there is disclosed a typical specimen of a tree of my new variety "Bridal Bouquet" which clearly discloses the very white color of the tree as it appears in full bloom and while it does not show in detail the individual flowers, it may be noted that they are obviously very abundant and provide a good show in a typical tree as disclosed, obviously also the tree being on a relatively small scale and depicted in color which is as nearly possible to represent the same in any color illustration such as is used here. The additional drawing discloses a typical branch of the tree of my new variety and the flowers thereof in greater detail.

There follows a detailed description of my new variety with color terminology related to that used in the Munsell Color Chart, published by Munsell Color Co., Inc. and denominated Nickerson Color Fan except where general color terms of ordinary dictionary significance are applicable and of course made by me according to my personal observations and judgment therefore.

It may be noted that interestingly enough the petals when in bud exhibit a deep pink color but in full bloom are pure white as disclosed.

Parentage: Seedling.

*Seed parent.*—Malus "Katherine", (an unpatented variety).

*Pollen parent.*—Not known.

Propagation: Holds its distinguishing characteristics through succeeding propagations by bud-grafting.

Locality where grown and observed: South Brunswick Township, N.J.

Tree: Small; spreading; low; hardy.

*Trunk.*—Stocky; rough.

*Branches.*—Slender; smooth. Color — Moderate reddish brown Munsell Color 2.5 YR 3/3. Lenticels — Sparse; inconspicuous.

Foliage:

*Leaves.*—Abundant; free from Apple Scab and Fire Blight diseases. Size — Length 6.5 to 7 cm. Width 3.5 to 4 cm. Shape — Oval; acuminate. Color — Upper surface dark yellowish green Munsell color 10GY 4/5. Lower surface moderate yellow green Munsell color 2.5 GY 5/5. Margin — Serrate. Petiole — Medium (3 to 4 cm. long). Glands — None. Stipules — Paired; minute; 0.5 cm. long.

Flower buds: Very hardy (to −20° F.).

*Size.*—Small; 0.2 cm. wide; 0.3 cm. long.

*Shape.*—Ovate; pointed.

*Color.*—Moderate brown; Munsell Color 5 YR 3/3.

Flowers: Double.

*Dates of first bloom.*—May 1 to 5.

*Dates of full bloom.*—May 5 to 10.

*Quantity.*—Very abundant.

*Size.*—Large; 4 to 5 cm. in diameter.

Petalage:

*Number.*—30 to 36.

*Shape of petals.*—Ovate.

*Size of petals.*—Length 2 to 2.4 cm. Width 1.4 cm.

*Color.*—In bud (Deep pink Munsell Color 2.5 R 6/11. In full bloom (Pure white.)

Fruits:

*When borne.*—Summer, lasting into late October.

*Abundance.*—Moderately abundant.

*Size.*—About 1.4 cm. long — 1.4 cm. wide.

*Color.*—Yellow with red blush on upper surface.

I claim:

1. A new and distinct variety of flowering Crab Apple Tree substantially as herein shown and described, characterized particularly as to novelty by the unique combination of the abundance, large size, and pure white color of its double flowers, further having extreme resistance to defoliation by Apple Scab disease as compared to other varieties of crab apple trees growing nearby, and not having any tendency to die back from Fire Blight disease even in wet summers.

* * * * *